United States Patent [19]

Hill et al.

[11] Patent Number: 5,198,598
[45] Date of Patent: Mar. 30, 1993

[54] TELOMERIZATION PROCESS OF A CONJUGATED ALKADIENE WITH A POLYOL

[75] Inventors: Karlheinz Hill, Erkrath, Fed. Rep. of Germany; Steven D. Axt, Cupertino; Kenneth J. Weese, Daly City, both of Calif.

[73] Assignee: Henkel Kommanditgesellschaft auf Aktien, Duesseldorf-Holthausen, Fed. Rep. of Germany

[21] Appl. No.: 732,551

[22] Filed: Jul. 19, 1991

[51] Int. Cl.[5] .............................................. C07C 43/11
[52] U.S. Cl. .................................... 568/619; 568/673; 568/675; 568/690
[58] Field of Search ................ 568/619, 673, 675, 690

[56] References Cited

U.S. PATENT DOCUMENTS

| | | | |
|---|---|---|---|
| 3,489,130 | 1/1970 | Dewhirst | 260/611 |
| 3,499,042 | 3/1970 | Smutney | 568/690 |
| 3,670,032 | 6/1972 | Romanelli | 260/614 AA |
| 3,746,749 | 7/1973 | Mitsuyasu et al. | 260/497 A |
| 3,769,352 | 10/1973 | Romanelli | 260/614 AA |
| 3,792,101 | 2/1974 | Hattori et al. | 260/677 R |
| 3,887,627 | 3/1975 | Romanelli | 568/840 |
| 3,891,684 | 6/1975 | Jung | 260/429 R |
| 3,923,875 | 12/1975 | Rose et al. | 260/497 A |
| 3,992,456 | 11/1976 | Atkins | 260/632 R |
| 4,006,192 | 2/1977 | Enomoto et al. | 568/690 |
| 4,142,060 | 2/1979 | Kuntz | 568/840 |
| 4,146,738 | 3/1979 | Jadamus et al. | 568/690 |
| 4,196,135 | 4/1980 | Enomoto et al. | 260/429 R |
| 4,219,677 | 8/1980 | Kuntz | 568/657 R |
| 4,260,750 | 4/1981 | Kuntz | 544/178 |
| 4,356,333 | 10/1982 | Yoshimura et al. | 568/840 |
| 4,417,079 | 11/1983 | Yoshimura et al. | 568/903 |
| 4,454,333 | 6/1984 | Jenck | 560/1 |
| 4,515,711 | 5/1985 | Chalk et al. | 252/522 |
| 4,522,760 | 6/1985 | Jenck | 260/410.9 R |
| 4,642,392 | 2/1987 | Hanes | 568/690 |

FOREIGN PATENT DOCUMENTS

| | | |
|---|---|---|
| 287066 | 10/1988 | European Pat. Off. |
| 1807491 | 6/1969 | Fed. Rep. of Germany |
| 2154370 | 5/1973 | Fed. Rep. of Germany |
| 2505180 | 8/1976 | Fed. Rep. of Germany |
| 47031906 | of 0000 | Japan |
| 49031965 | of 0000 | Japan |
| 49048613 | of 0000 | Japan |
| 49125313 | of 0000 | Japan |
| 50157301 | of 0000 | Japan |
| 51008206 | of 0000 | Japan |
| 51142532 | of 0000 | Japan |
| 51149206 | of 0000 | Japan |
| 57007426 | of 0000 | Japan |
| 73003605 | of 0000 | Japan |
| 73042606 | of 0000 | Japan |
| 74046286 | of 0000 | Japan |
| 1248592 | 10/1971 | United Kingdom |
| 1248593 | 10/1971 | United Kingdom |
| 1354507 | 5/1974 | United Kingdom |
| 2054394 | 2/1981 | United Kingdom |
| 2114974 | 9/1983 | United Kingdom |

OTHER PUBLICATIONS

Behr, "Organometallics" 5, 514–8 (1986).
Jolly, "Organometallics" 5, 473–81 (1986).
Dzhemilev, "Zh. Org. Khim." 22(8), 1591–7 (1986).
Behr, "Organometallics" 4, 1945–53 (1985).
Bochmann, "J. Molec. Catalysis" 26, 79–88 (1984).
Behr, "Aspects of Homogeneous Catalysis" 5, 5–58 (1984).
Groult, "Tetrahedron" 39, (9) 1543–50 (1983).
Kaneda, "J. Org. Chem." 46, 2356–62 (1981).
Dzhemilev, "Izv. Akad. Nauk. SSSR, Ser. Khim." 8, 1837–425 (1981).
Bianchini, "J. Molec. Catalysis" 10, 247–252 (1981).
Dzhemilev, "Zh. Org. Khim," 16 (6), 1157–61 (1980)(translation).
Tamuro, "Tetr. Letters" 21, 3787–90 (1980).
Tsuji, "Pure & Appl. Chem." 51, 1235–41 (1979).
Kluter, "J. Organomet. Chem." 137 (3), 309–14 (1977).
Baker, "Chemical Reviews" 73 (5), 503–9 (1973).
Tsuji, "Accounts Chem. Res." 6 (1), 8–15 (1973).
Smutny, "Annals N.Y. Acad. Sci." 214, 124–142 (1973).
Rose, "J. Organometallic Chem." 49, 473–6 (1973).
Smutny, "ACS, Div. Pet. Chem.", Prepn. 14 (2), B100–11 (1969).
Takahashi, "Bull. Chem. Soc. Japan" 41, 254–5 (1968).
Takahashi, "Bull. Chem. Soc. Japan" 41, 454–60 (1968).
Smutny, "J. Am. Chem. Soc." 89, 6793–4 (1967).
Takahashi, "Tetr. Letters" (26), 2451–3 (1967).

*Primary Examiner*—Marianne M. Cintins
*Assistant Examiner*—Rebecca Cook
*Attorney, Agent, or Firm*—Wayne C. Jaeschke; Henry E. Millson, Jr.; John E. Drach

[57] ABSTRACT

Alkadienyl ethers are prepared by the telomerization of conjugated dienes with polyols by continuous addition of the alkadiene to a reaction mixtue comprised of the polyol, secondary alcohol solvent, a portion of the alkadiene to be added, and low palladium catalyst concentration.

18 Claims, No Drawings

TELOMERIZATION PROCESS OF A CONJUGATED ALKADIENE WITH A POLYOL

BACKGROUND OF THE INVENTION

1. Field of the Invention

This invention relates to a process for telomerizing a conjugated alkadiene with a polyol.

2. Statement of Related Art

It is known in the art that conjugated alkadienes can telomerize with alcohols to give 1,7- and 2,7-alkadienyl ethers. The following references exemplify extensive patent and other literature that relate to such telomerization reactions and novel compounds prepared by such reactions: U.S. Pat. Nos. 3,489,813; 3,499,042; 3,670,032; 3,769,352; 3,792,101; 3,887,627; 3,891,684; 3,923,875; 3,992,456; 4,006,192; 4,142,060; 4,146,738; 4,196,135; 4,219,677; 4,260,750; 4,356,333; 4,417,079; 4,454,333; 4,515,711; 4,522,760; and 4,642,392. British Patent Nos. 1,248,592; 1,248,593; 1,354,507; 2,054,394; and 2,114,974. German Patent Nos. 1,807,491; 2,154,370; and 2,505,180. Japanese Patent Nos. 72,020,604; 47,031,906; 48,039,413; 73,042,606; 73,003,605; 49,031,965; 49,048,613; 49,125,313; 74,046,286; 50,157,301; 51,008,206; 51,142,532; 51,149,206; and 51,007,426. Literature articles: Behr, Organometallics 5, 514–8 (1986) Jolly, Organometallics 5, 473–81 (1986) Dzhemilev, Zh. Org. Khim. 22 (8), 1591–7 (1986) Gaube, J. Prakt. Chim. 327 (4), 643–8 (1985) Jolly, Organometallics 4, 1945–53 (1985) Bochmann, J. Molec. Catalysis 26, 79–88 (1984) Behr, Aspects of Homogeneous Catalysis 5, 5–58 (1984) Gaube, J. Prakt. Chem. 326, (6) 947–54((1984) Behr, Chem. Ber. 116, 862–73 (1983) Groult, Tetrahedron 39, (9) 1543–50 (1983) Teranishi, J. Org. Chem. 46, 2356–62 (1981) Dzhemilev, Izv. Akad. Nauk. SSSR, Ser. Khim. 8, 1837–425 (1981) Keim, J. Molec. Catalysis 10, 247–252 (1981) Dzhemilev, Zh. Org. Khim. 16 (6), 1157–61 (1980) Yoshida, Tetr. Letters 21, 3787–90 (1980) Tsuji, Pure & Appl. Chem. 51, 1235–41 (1979) Tsuji, Adv. in Organometallic Chem. 17, 141–93 (1979) Singer, J. Organomet. Chem. 137 (3), 309–14 (1977) Chauvin, Tet. Letters 51, 4559–62 (1975) Chauvin, Bull. Soc. Chim. Fr. 652–6 (1974) Beger, J. prakt. Chem. 315 (6), 1067–89 (1973) Baker, Chemical Reviews 73 (5), 503–9 (1973) Tsuji, Accounts Chem. Res. 6 (1), 8–15 (1973) Smutny, Annals N.Y. Acad. Sci. 214, 124–142 (1973) Chauvin, Tetr. Letters 51, 4559–62 (1973) Rose, J. Organometallic Chem. 49, 473–6 (1973) Smutny, ACS, Div. Petr. Chem., Prepn. 14 (2), B100–11 (1969) Takahashi, Bull. Chem. Soc. Japan 41, 254–5 (1968) Takahashi, Bull. Chem. Soc. Japan 41, 454–60 (1968) Smutny, J. Am. Chem. Soc. 89, 6793–4 (1967) Takahashi, Tetr. Letters (26), 2451–3 (1967).

The process according to the invention produces alkadienyl ethers of polyols which are commercially important materials useful as emulsifiers, lubricants, and thickening agents. British patent application No. 2,054,394 discloses the preparation of the di-1-(2,7-octadienyl) ether of ethylene glycol; Zh. Org. Khim. 16 (6), 1157–61 (1980) discloses the preparation of the mono- and di-1-(2,7-octadienyl) ethers of 1,4-butanediol, 1,2-propylene glycol, glycerol, and the mono-1-(2,7-octadienyl) ether of 2-hydroxyethoxyethanol; British patent No. 1,354,507 discloses the preparation of 1-(2,7-octadienyl) ether of methanol; Japanese patent No. JP 49,031,965 discloses the mono-1-(2,7-octadienyl) ether of ethylene glycol.

These alkadienyl ethers are most readily prepared by the telomerization of a conjugated alkadiene by alcohols in the presence of palladium catalysts. However, the development of economically practical telomerization processes has not been achieved primarily because of the cost of the palladium catalysts. The prior art contains many examples of attempts to deal with the catalyst cost problem. For example, U.S. Pat. No. 4,642,392 discloses a catalyst recovery method which employs the use of a high boiling reaction solvent which allows for the distillation of the product telomer leaving behind catalyst solution which can be reused many times with, presumably, minimum palladium loss. Other catalyst recovery methods are disclosed in U.S. Pat. Nos. 4,454,333; 4,552,760; 4,260,750; 4,219,667; 4,142,060; 4,417,079; 4,356,333; Japanese patent No. 50,157,301; 51,149,206.and British patent No. 2,054,394. All of the above catalyst recovery schemes require additional process operations which add to the cost of the final product.

The use of low palladium levels in the telomerization of conjugated dienes is disclosed in British patent No. 2,114,974. This patent teaches that when 1,4-butanediol, 1,5-pentanediol, and 1,6-hexanediol telomerized with butadiene, about a 61% yield of monoether based on butadiene can be realized by using a molar ratio of catalyst/diene equal to about 1/20,600. The patent also discloses that a large stoichiometric excess of diol is also necessary in order to obtain high yields of the desired monoether product. For best yields of monoether, the above patent also teaches that the optimum catalytic effect is obtained by combining the palladium catalyst with a nickel(II) compound and a base such as a quaternary ammonium hydroxide. The patent also discloses a method of removing the palladium catalyst with ion exchange resins from the reaction mixture after the reaction has been completed. The palladium levels are obviously not low enough to preclude the recovery step; an operation which the present invention eliminates. U.S. Pat. No. 3,746,749 discloses that octadienyl esters of adipic acid can be prepared in 86% yield by employing a molar ratio of Pd/Acid/Butadiene equal to 1/12,300/56,000 and octadienyl esters of fumaric acid can be prepared in 67% yield by employing a molar ratio of Pd/Acid/Butadiene equal to 1/60,000/28,000. However, these low palladium levels are used in conjunction with from 0.1 to 10 moles of an alkali metal salt of a carboxylic acid/mole of carboxylic acid. U.S. Pat. No. 4,417,079 teaches the telomerization of butadiene with water containing $CO_2$ to produce octadienyl alcohol by introducing liquified butadiene continuously at the rate of 70 grams per hour at 80° C. for an hour. EP 287,066 teaches the telomerization of butadiene with water in a solvent such as sulfolane by continuous addition of butadiene to give a decreased amount of insoluble polymer. U.S. Pat. No. 4,146,738 teaches telomerization of a diolefin with a $C_{1-8}$ alkanol in the presence of a palladium catalyst system in which the number of phosphine ligands is controlled by oxidation The diolefin is added such that it is replenished as it is consumed either in incremental portions or continuously as indicated by pressure drop. The patent further teaches in example 5 that the non-continuous addition of butadiene to isopropanol at a Pd/butadiene ratio equal to 1/3760 produces a product which is 49% octatriene in an overall yield based on butadiene of about 45%. In example 7 which employs the same reaction conditions as example 5, butadiene is added continuously. The product contains a large percentage of the octadienyl ether of isopropanol and a greatly diminished amount of octatriene (1.6%) but the total product yield based on butadiene decreased to about 31%. The process according to the present invention produces high yields of the octadienyl ethers of polyols while utilizing a Pd/butadiene ratio of no more than 1/10,000 in the presence of a secondary alcohol such as isopropanol as a solvent. The product contains only a small amount of octadienyl ether of the secondary alcohol solvent and less than about 12% by weight octatriene but in a yield based on alkadiene of greater than 80%. The process according to the present invention utilizes significantly lower amounts of expensive palladium catalyst and an alcohol solvent. The process according to the invention surprisingly produces little of the octadienyl ether of secondary alcohol solvent. GB 1,248,593 teaches the telomerization of butadiene with alkanols in the presence of a palladium catalyst. It is not clear whether the patent teaches a continuous addition of butadiene. For instance, in example 6, methanol is reacted "under a butadiene atmosphere for 4 hours at 30° C. The initially slow absorption increased steadily." The Pd/butadiene ratio employed is about 1/1,000. J. prakt. Chemie 315, 1067–76 (1973) teaches the continuous reaction of ethanol with butadiene in the presence of a palladium catalyst wherein the Pd/butadiene ratio is about 1/10,000. The yield of the octadienyl ether of ethanol is about 9.4% based on butadiene. U.S. Pat. No. 4,006,192 discloses the preparation of the di- and tri-1-(2,7-octadienyl) ethers of trimethylolpropane by reaction of trimethylolpropane and butadiene using a catalyst prepared from palladium compounds, alkali metal salts of weak acids and phosphines. The teaching includes the disclosure that the Pd/butadiene ratio can be equal to from 1/1,000 to 1/100,000 and that the butadiene is added all at once. About 24% by weight of octatriene is formed along with the mono-, di- and tri-1-(2,7-octadienyl) ethers of trimethylolpropane.

The process of the present invention overcomes the disadvantages of the prior art processes by adding the major portion of the alkadiene to reaction mixture comprised of a secondary alcohol solvent, a minor portion of the alkadiene to be added, and a palladium catalyst in amounts low enough to allow the catalyst to remain in the final reaction product without the need for recovery thereby making the process economically feasible for large scale production of alkadienyl ethers. At the same time, the process according to the invention produces high yields of octadienyl ether product and minimizes the production of alkadiene dimer side product.

SUMMARY OF THE INVENTION

The present invention relates to a process for producing alkadienyl ethers of polyols which are useful as surfactants, as emulsifiers, as components for cosmetics, as PVC lubricants and as precursors for polymers. The process according to the invention comprises continuously adding a conjugated alkadiene to a reaction mixture which contains at least one polyol, a saturated aliphatic secondary alcohol solvent, a catalyst effective amount of a palladium catalyst, and less than about 40% by weight of the total amount of alkadiene to be added. The remainder of the alkadiene is added at a temperature in the range of from about 40° C. to about 100° C. at a rate sufficient to maintain a constant pressure or at a constant rate over a period of from about 2 hours to about 10 hours. The palladium catalyst is present in a mole ratio of catalyst to diene of up to about 1:10,000. The process produces a reaction product in at least an 80% yield based on the moles of conjugated alkadiene consumed in the reaction, while the consumption of alkadiene in the reaction is at least 70% based on the total amount of the alkadiene added. The reaction product is comprised of less than about 12% by weight alkadiene dimer.

DESCRIPTION OF THE PREFERRED EMBODIMENTS

Other than in the operating examples, or where otherwise indicated, all numbers expressing quantities of ingredients or reaction conditions used herein are to be understood as modified in all instances by the term "about".

For purposes of the present invention, a polyol is any compound having two or more alcohol functionalities. This definition includes aliphatic and aromatic polyols such as ethylene glycol, 1,2-propanediol, 1,3-propanediol, 1,2-butanediol, 1,3-butanediol, 1,4-butanediol, 1,5-pentanediol, 1,6-hexanediol, 1,10-decanediol, 1,12-dodecanediol, 2-methyl-1,2-propanediol, 2,2-dimethyl-1,3-propanediol, glycerol (1,2,3-propanetriol), trimethylolpropane (2-ethyl-2-(hydroxymethyl)-1,3-propanediol), pentaerythritol (2,2-dimethylol-1,3-propanediol), diglycerol (glycerol dimer), bis-phenol A and the like. The preferred polyols are ethylene glycol, glycerol, trimethylolpropane, and 1,2-propanediol.

The conjugated alkadienes that can be employed in the process of the present invention include branched or straight chain aliphatic conjugated dienes containing from 4 to 20 carbon atoms, or cyclic dienes containing from 6 to 8 carbon atoms, and which may optionally be substituted with one or more inert groups such as $C_1$–$C_8$ alkyl groups, phenyl, cyclohexyl, nitro, oxo, alkoxycarbonyl having 1 to 4 carbon atoms in the alkyl group, or halogen such as fluorine or chlorine wherein the halogen is in a position inert to the process conditions, for example, chloroprene. Other conjugated dienes that can be used in the process of this invention include 1,3-butadiene, dimethylbutadiene, isoprene, piperylene, 1,3-hexadiene, 2,4-hexadiene, chloroprene, 1-cyclohexyl-1,3-butadiene, 1-phenyl-1,3-butadiene, 2,4-octadiene, 2-methyl-2,4-pentadiene, 1,3-cyclohexadiene, and 1,3-cyclooctadiene. The preferred conjugated alkadiene is 1,3-butadiene.

The secondary alcohol solvents which can be used in the process according to the invention are saturated aliphatic alcohols having from 3 to 10 carbon atoms preferably 3 to 4 carbon atoms such 2-propanol or 2-butanol. The preferred secondary alcohol solvent is isopropyl alcohol (2-propanol). Mixtures of two or more secondary alcohol solvents can also be used. The secondary alcohol solvent can also contain water as a cosolvent in those cases where the glycol may not be completely soluble in the secondary alcohol solvent. An example of such a situation is when pentaerythritol is used as the telogen in the telomerization of 1,3-butadiene. The amount of secondary alcohol solvent will vary between 5 and 200 weight percent based on the weight of polyol. The preferred amount is from about 10 to about 150 weight percent based on the weight of polyol.

The ratio of polyol reactant to conjugated alkadiene reactant depends upon the degree of etherification desired in the final product. For example, if a product comprised of predominantly the mono-alkadienyl ether of a polyol is desired, then a polyol/alkadiene mole ratio of about ½ should be employed. The skilled artisan can easily determine the optimum polyol/alkadiene mole ratio to be used to realize the optimum yield of desired product. It is understood that the determination of the optimum polyol/alkadiene mole ratio must include a consideration of the number of alcohol functionalities in a particular polyol and the possible reactivity differences between primary, secondary, and tertiary alcohol groups.

The catalyst used in the process according to the invention is a catalyst system comprised of a palladium compound and a cocatalyst. The palladium catalysts are selected from the group consisting of palladium acetylacetonate [Pd(acac)$_2$], bis(allyl)palladium [Pd(C$_3$H$_5$)$_2$], bis(cyclooctadiene)palladium [Pd(COD)$_2$], palladium chloride (PdCl$_2$), palladium acetate [Pd(OAc)$_2$], and allyl palladium chloride [Pd(C$_3$H$_5$)Cl]. The cocatalysts are selected from the group consisting of trialkylphosphine, triarylphosphine, or triarylphosphite. A mixture of alkyl, aryl, or aryl/alkyl phosphines and phosphites can also be used. Examples of trialkylphosphines include triethylphosphine and tributylphosphine. Examples of triarylphosphines include triphenylphosphine, o-,m-,p-tolylphosphine, 1,2-bis(diphenylphosphino)ethane, and 1,2- bis(di-p-tolylphosphino)ethane. Examples of triarylphosphites include tri(o-tolyl)phosphite, triphenylphosphite, trimethylphosphite, and triethylphosphite. Another suitable catalyst is tetrakis(triphenylphosphine)palladium [Pd(PPh$_3$)$_4$].

The most preferred catalyst systems are complexes of the acetylacetonate of Pd(II) with two equivalents of triphenylphosphine as a ligand, palladium(II) acetate with two equivalents of triphenylphosphine as a ligand, palladium(II) chloride with two equivalents of triphenylphosphine as a ligand, and tetrakis(triphenylphosphine)palladium.

The mole ratio of palladium catalyst to conjugated alkadiene is from about 1:10,000 to about 1:200,000. The optimum ratio for any particular system will depend upon a number of factors and can be determined by the skilled artisan. A preferred amount is from about 1:25,000 to about 1:150,000 while a most preferred amount is from 1:100,000 to about 1:130,000.

The process according to the invention is achieved without the addition of a catalyst reductant such as triethylaluminum or sodium borohydride, which are often used in the prior art processes. The catalyst used herein is preferably prepared by combining a palladium catalyst with two equivalents of a cocatalyst in the polyol reactant to be used in the process.

The process according to the invention can be carried out in any suitable reaction vessel, such as a glass autoclave, steel autoclave, or any other reaction vessel equipped for reactions under pressure.

The process according to the invention can be carried out in a range of from about 40° to 100° C. preferably in the range of from 60° C. to 80° C.

The general procedure for carrying out the process of the present invention involves introducing the palladium catalyst-polyol-secondary alcohol mixture into a pressure reactor. The reactor is then flushed with an inert gas such as nitrogen, evacuated and repressurized with about 5% to about 40% by weight of the total amount of alkadiene to be added. Preferably, the initial amount of alkadiene is about 10% by weight of the total amount of alkadiene to be added. The contents of the reactor can then be heated to an appropriate reaction temperature in the range of from about 40° C. to about 100° C. afterwhich the remainder of the alkadiene is added at a rate sufficient to maintain the autogenous pressure developed after the reaction has commenced. For example, if after adding the initial amount of diene, the reaction temperature is raised to 70° C. and after the reaction has started as indicated by a pressure drop to 35 psig, the remainder of the alkadiene is added at a rate sufficient to maintain the pressure at about 35 psig. Alternatively, the remaining alkadiene can be added at a constant rate over a period of from about 2 hours to about 10 hours at a temperature of from about 40° C. to about 100° C. at whatever pressure is developed during the addition. The reaction temperature is maintained in the range of from about 40° C. to about 100° C. after all the diene has been added for a period of from about 0.5 to about 20 hours or for such time as is necessary to react the remaining amounts of diene. The progress of the reaction can be followed by periodic analysis of the reaction mixture such as by gas chromatography (Gas chromatographic conditions are given in Example 1).

The reaction products are isolated by standard techniques such as distillation, crystallization or filtration.

The following examples are meant to illustrate but not to limit the invention.

EXAMPLE 1

Telomerization of 1,3-Butadiene with Glycerol by Continuous Addition of 1,3-Butadiene To a four liter autoclave equipped with a stirrer, there was added 0.0854 grams (0.28 mmol) of palladium(II) acetylacetonate, 0.146 grams (0.557 mmol) of triphenylphosphine, 463 grams (5.03 mol) of glycerol, and 575 grams of 2-propanol. The autoclave was sealed and agitation begun and maintained at 600 rpm throughout the course of the reaction. The reactor was degassed by evacuating to −15 psig, purged with nitrogen to 30 psig and vented. After the degassing-purging cycle was accomplished two more times, the reactor was left evacuated. A cylinder containing about 1134 grams of butadiene (21 moles) was briefly opened to the reactor so that about 113 grams were added. The reactor was then heated to about. 70° C. and the internal pressure rose to 55 psig. After the internal pressure in the reactor rose above that of the butadiene cylinder, the butadiene cylinder was opened to the reactor through a one-way valve. After about 75 minutes at 70° C., the cylinder was pressurized to 25-35 psig with nitrogen. The pressure remained constant thereafter until all the butadiene had been added. After a total time of about 10 hours, the reaction mixture was cooled to room temperature. The total weight of the cooled reaction mixture was 2075 grams which was stripped under vacuum to about 1204 grams. Gas chromatographic analysis of the crude reaction mixture prior to stripping showed the following percentages by area percent: 10% octatriene; 6% isopropyloctadienyl ether; 25% glycerol-mono-octadienyl ether; 50% glycerol-di-octadienyl ethers; and 9% glycerol-tri-octadienyl ethers. In this and subsequent examples, gas chromatographic analysis was carried out with a Hewlett-Packard 5890 gas chromatograph with a 7673 autoinjector and a flame ioinzation detector. A Supelco SBP-5 column (15 m × 320 μm i.d.) was used with a 50 kPa head pressure. The injection port as set at 300° C. and the detector at 325° C. The temperature program was as follows: after 1.0 minutes at 40° C. the oven temperature was ramped at 10°

C./minute to 270° C. and held for 2.0 minutes. The isopropyl alcohol peak was rejected in all analyses.

EXAMPLE 2

Telomerization of 1,3-Butadiene with Glycerol by All-At-Once Addition of 1,3-Butadiene The procedure of Example 1 was repeated except that the butadiene was added at one time. After addition of the butadiene and heating the reaction mixture to 70° C., the internal pressure rose to a maximum of 115 psig and decreased slowly throughout the reaction period. After a total time of about 9.5 hours, the reaction mixture was cooled to room temperature. The total weight of the cooled reaction mixture was 1986 grams which was stripped under vacuum to about 1211 grams. Gas chromatographic analysis of the reaction mixture showed the following percentages by area percent: 18% octatriene; 5% isopropyloctadienyl ether; 21% glycerol-mono-octadienyl ether; 47% glycerol-di-octadienyl ethers; and 8% glycerol-tri-octadienyl ethers.

EXAMPLE 3

Telomerization of 1,3-Butadiene with Ethylene Glycol by Continuous Addition of 1,3-Butadiene The procedure of Example 1 was repeated except that a 500 ml autoclave was used and 0.0183 grams (0.060 mmol) of palladium(II) acetylacetonate, 0.0315 grams (0.12 mmol) of triphenylphosphine, 93 grams (1.5 mol) of ethylene glycol, and 16 grams of 2-propanol were used. The total amount of butadiene added was 260 grams (4.8 mol). The reaction was terminated after 12 hours. The total weight of the reaction mixture after venting excess butadiene was 1580 grams (80% conversion of butadiene). Gas chromatographic analysis of the crude reaction mixture prior to stripping showed the following percentages by area percent: 4% ethylene glycol; 6% octatriene; 1% isopropyloctadienyl ether; 1% ethylene glycol-mono-octadienyl ether; 55% ethylene glycol-di-octadienyl ethers.

EXAMPLE 4

Telomerization of 1,3-Butadiene with Ethylene Glycol by Continuous Addition of 1,3-Butadiene in the Absence of Alcohol Solvent The same procedure and amounts of reactants as in Example 3 was repeated except that the reaction temperature was maintained in the 60° C.–67° C. range. The total weight of the reaction mixture after venting excess butadiene was 845 grams (29% conversion of butadiene). Gas chromatographic analysis of the reaction mixture showed the following percentages by area percent: 22% ethylene glycol; 1.7% octatriene; 63% ethylene glycol-mono-octadienyl ether; 14% ethylene glycol-di-octadienyl ethers.

EXAMPLE 5

Telomerization of 1,3-Butadiene with Ethylene Glycol by Continuous Addition of 1,3-Butadiene in the Absence of Alcohol Solvent and Wherein the Addition is Begun at 50° C.

The same procedure as in Example 3 was repeated except that the continuous addition of butadiene was not started until a temperature of at least 50° C. was reached and 0.024 grams (0.0785 mmol) of palladium(II) acetylacetonate, 0.041 grams (0.156 mmol) of triphenylphosphine, 60.5 grams (0.975 mol) of ethylene glycol were used and no isopropanol was used and all of the butadiene was added at 50° C. The total amount of butadiene added was 167 grams (3.1 mol). The total weight of the reaction mixture after venting excess butadiene was 64 grams (2% conversion of butadiene).

EXAMPLE 6

Telomerization of 1,3-Butadiene with Ethylene Glycol by All-At-Once Addition of 1,3-Butadiene The same procedure as in Example 3 was repeated except that the reaction was carried out in a 500 ml autoclave using 0.0038 grams (0.125 mmol) of palladium(II) acetylacetonate, 0.0066 grams (0.025 mmol) of triphenylphosphine, 9.6 grams (0.155 mol) of ethylene glycol. The total amount of butadiene added was 26 grams (0.488 mol) added all at once at room temperature. The autoclave was closed and the reaction temperature increased to 70° C. After 14.5 hours of reaction time the reaction mixture was cooled to room temperature and the excess butadiene was vented. The total weight of the reaction mixture after venting excess butadiene was 32.5 grams (87% conversion of butadiene). Gas chromatographic analysis of the reaction mixture prior to stripping showed the following percentages by area percent: 2% ethylene glycol; 14% octatriene; 50% ethylene glycol-mono-octadienyl ether; 34% ethylene glycol-di-octadienyl ethers.

What is claimed is:

1. A process for the telomerization of a conjugated alkadiene with a polyol comprising the steps of: (a) providing a reaction mixture comprised of at least one polyol reactant, at least one saturated aliphatic secondary alcohol solvent, and a catalyst effective amount of a palladium catalyst and adding a conjugated alkadiene to said mixture, wherein said palladium catalyst is present in a mole ratio of palladium catalyst to total alkadiene of up to about 1:10,000, and wherein said reaction mixture contains from about 5% to about 40% by weight of the total amount of conjugated alkadiene to be added; (b) heating said reaction mixture to from about 40° C. to about 100° C.; (c) continuously adding the remaining amount of said conjugated diene to said reaction mixture at a rate sufficient to maintain a constant pressure or at a constant rate over a period of from about 2 hours to about 10 hours at a temperature of from about 40° C. to about 100° C. to produce a reaction product comprised of less than about 12% by weight alkadiene dimer.

2. The process of claim 1 wherein said palladium catalyst is selected from the group consisting of acetylacetonate of Pd(II) with two equivalents of triphenylphosphine as a ligand, palladium(II) acetate with two equivalents of triphenylphosphine as a ligand, palladium(II) chloride with two equivalents of triphenylphosphine as a ligand, and tetrakis(triphenylphosphine)palladium.

3. The process of claim 2 wherein said palladium catalyst is acetylacetonate of Pd(II) with two equivalents of triphenylphosphine.

4. The process of claim 1 wherein said mole ratio of palladium catalyst to diene is from about 1:25,000 to about 1:200,000.

5. The process of claim 4 wherein said mole ratio of palladium catalyst to diene is from about 1:70,000 to about 1:130,000.

6. The process of claim 1 wherein said conjugated diene is a branched- or straight-chain aliphatic diene having from 4 to 20 carbon atoms or a cyclic diene having from 5 to 8 carbon atoms.

7. The process of claim 6 wherein said conjugated diene is 1,3-butadiene, piperylene, isoprene, or mixtures thereof.

8. The process of claim 7 wherein said conjugated diene is 1,3-butadiene.

9. The process of claim 1 wherein said process is carried out at a temperature of from about 60° C. to about 80° C.

10. The process of claim 1 wherein said secondary alcohol solvent is 2-propanol.

11. The process of claim 1 wherein said polyol is glycerol.

12. The process of claim wherein said polyol is trimethylolpropane.

13. The process of claim 1 wherein the amount of alkadiene present in said reaction mixture in step (a) is about 10% by weight of the total amount of alkadiene to be added.

14. A process for the telomerization of a conjugated alkadiene which is a branched- or straight-chain aliphatic diene having from 4 to 20 carbon atoms or a cyclic diene having from 5 to 8 carbon atoms with a polyol comprising the steps of: (a) providing a reaction mixture comprised of at least one polyol reactant, at least one saturated aliphatic secondary alcohol solvent, and a catalyst effective amount of a palladium catalyst and adding a conjugated alkadiene to said mixture, wherein said palladium catalyst is present in a mole ratio of palladium catalyst to total alkadiene of from about 1:70,000 to about 1:130,000 and wherein said reaction mixture contains from about 5% to about 40% by weight of the total amount of conjugated alkadiene to be added; (b) heating said reaction mixture to from about 60° C. to about 80° C.; (c) continuously adding the remaining amount of said conjugated diene to said reaction mixture at a rate sufficient to maintain a constant pressure or at a constant rate over a period of from about 2 hours to about 10 hours at a temperature of from about 60° C. to about 80° C. to produce a reaction product comprised of less than about 12% by weight alkadiene dimer.

15. The process of claim 14 wherein said palladium catalyst is selected from the group consisting of acetylacetonate of Pd(II) with two equivalents of triphenylphosphine as a ligand, palladium(II) acetate with two equivalents of triphenylphosphine as a ligand, palladium(II) chloride with two equivalents of triphenylphosphine as a ligand, and tetrakis(triphenylphosphine) palladium.

16. The process of claim 14 wherein said conjugated diene is 1,3-butadiene, piperylene, isoprene, or mixtures thereof.

17. The process of claim 14 wherein said polyol is glycerol or trimethylolpropane.

18. The process of claim 16 wherein said polyol is glycerol or trimethylolpropane.

* * * * *